(12) United States Patent
Kang et al.

(10) Patent No.: US 12,409,346 B2
(45) Date of Patent: Sep. 9, 2025

(54) ULTRASOUND-BASED MICROPARTICLE TRAPPING AND STIMULATION DEVICE

(71) Applicant: KOREA INSTITUTE OF MEDICAL MICROROBOTICS, Gwangju (KR)

(72) Inventors: Byung Jeon Kang, Gwangju (KR); Jong Oh Park, Gyeonggi-do (KR); Chang Sei Kim, Gwangju (KR); Eun Pyo Choi, Gwangju (KR); Do Yeon Bang, Gwangju (KR); Han Sol Lee, Gwangju (KR)

(73) Assignee: KOREA INSTITUTE OF MEDICAL MICROROBOTICS, Gwangju (KR)

( * ) Notice: Subject to any disclaimer, the term of this patent is extended or adjusted under 35 U.S.C. 154(b) by 162 days.

(21) Appl. No.: 18/269,993

(22) PCT Filed: Jan. 4, 2022

(86) PCT No.: PCT/KR2022/000035
§ 371 (c)(1),
(2) Date: Jun. 28, 2023

(87) PCT Pub. No.: WO2022/146122
PCT Pub. Date: Jul. 7, 2022

(65) Prior Publication Data
US 2024/0058626 A1    Feb. 22, 2024

(30) Foreign Application Priority Data

Jan. 4, 2021 (KR) .......................... 10-2021-0000526

(51) Int. Cl.
*A61B 34/00* (2016.01)
*A61B 34/30* (2016.01)
(Continued)

(52) U.S. Cl.
CPC ................ *A61N 7/02* (2013.01); *A61B 34/30* (2016.02); *A61B 34/70* (2016.02); *A61K 9/0009* (2013.01);
(Continued)

(58) Field of Classification Search
CPC .............. A61N 7/02; A61N 2007/0078; A61N 2007/0091; A61N 2007/0065;
(Continued)

(56) References Cited

U.S. PATENT DOCUMENTS

| 6,216,538 B1 | 4/2001 | Yasuda et al. |
| 2018/0071505 A1 | 3/2018 | Lo et al. |

(Continued)

FOREIGN PATENT DOCUMENTS

| JP | 2004-507280 A | 3/2004 |
| KR | 101533402 B1 | 7/2015 |
| KR | 10-2020-0101162 A | 8/2020 |

OTHER PUBLICATIONS

Nakahara, J., et al.; "Contact-less Manipulation of Millimeter-scale Objects via Ultrasonic Levitation", 2020 8th IEEE International Conference on Biomedical Robotics and Biomechatronics (BioRob), New York, USA, Nov. 29, 2020-Dec. 1, 2020, pp. 264-271.

(Continued)

*Primary Examiner* — Michael J Carey
*Assistant Examiner* — Zainab Mohammed Aldarraji
(74) *Attorney, Agent, or Firm* — Harness, Dickey & Pierce, P.L.C.

(57) ABSTRACT

The present invention relates to an ultrasound-based microparticle trapping and stimulation device. A transducer array system, according to the present invention, focuses high-intensity ultrasonic waves in a focal region, and at the same time, has an outstandingly excellent effect of being capable of capturing microparticles by means of low pres- (Continued)

sure inside a pressure field, and thus may be used in various medical fields.

12 Claims, 11 Drawing Sheets

(51) Int. Cl.
*A61K 9/00* (2006.01)
*A61K 41/00* (2020.01)
*A61N 7/00* (2006.01)
*A61N 7/02* (2006.01)

(52) U.S. Cl.
CPC ............... *A61K 41/0028* (2013.01); *A61N 2007/0078* (2013.01); *A61N 2007/0091* (2013.01)

(58) Field of Classification Search
CPC ................ A61N 2007/0095; A61B 34/30; A61B 34/70; A61B 1/00; A61B 17/00; A61B 1/00147; A61B 2017/00345; A61B 2034/303; A61K 9/0009; A61K 41/0028; A61K 9/51

See application file for complete search history.

(56) References Cited

U.S. PATENT DOCUMENTS

2021/0038925 A1* 2/2021 Emery ................. A61B 8/4209
2022/0175357 A1* 6/2022 Ding ......................... A61N 7/02

OTHER PUBLICATIONS

International Search Report from corresponding PCT Application No. PCT/KR2022/000035, dated Apr. 22, 2022.

* cited by examiner

2000

2000

Phase difference : 0     Phase difference : π

ULTRASOUND-BASED MICROPARTICLE TRAPPING AND STIMULATION DEVICE

CROSS-REFERENCE TO RELATED APPLICATIONS

This application is a national phase application of PCT Application No. PCT/KR2022/000035, filed Jan. 4, 2022, which claims benefit of Korean Patent Application No. 10-2021-0000526, filed on Jan. 4, 2021. The entire disclosures of the applications identified in this paragraph are incorporated herein by references.

TECHNICAL FIELD

The present disclosure was made with the support of the Ministry of Science and ICT, the Ministry of Trade, Industry and Energy, the Ministry of Health and Welfare, and the Ministry of Food and Drug Safety of the Republic of Korea under Project ID No. 1415184155 and Sub-Project No. RS-2021-KD000001. This research was conducted by the Korea Institute of Medical Microrobotics as part of the program titled "Development of a Medical Device for Active and Precise Delivery of Therapeutic Substances Based on Microcarriers for Knee Cartilage Regeneration." It falls under the broader research project "Korea Medical Device Development Project," managed by the Korea Medical Device Development Fund (KMDF). The project was carried out with a contribution rate of 50% from Jan. 1, 2024, to Dec. 31, 2024.

The present disclosure was made with the support of the Ministry of Trade, Industry & Energy (MOTIE) of the Republic of Korea under Project ID No. 1415180101 and Sub-Project No. 20017903. This research was conducted by the Korea Institute of Medical Microrobotics as part of the program titled "A Convergent Medical Device for Active and Precise Delivery of Embolic Particles in Transarterial Chemoembolization for Liver Tumor Treatment and a Simulator for Embolization Training." It falls under the broader research project "Biotechnology Industry Technology Development Project," managed by the Korea Planning & Evaluation Institute of Industrial Technology (KEIT). The project was carried out with a contribution rate of 50% from Jan. 1, 2024, to Dec. 31, 2024.

The present disclosure relates to an ultrasound-based microparticle trapping and stimulation device and, more particularly, to a device for trapping or stimulating microparticles by adjusting a phase difference between a first transducer disposed in a central area and a second transducer disposed to surround an outer circumference of the first transducer.

BACKGROUND ART

As conventional ultrasonic transducers, a high-intensity focused ultrasound (HIFU) transducer and an ultrasonic transducer array for particle trapping are generally used.

High-intensity focused ultrasound includes a single-element transducer that forms a focus through surface curvature thereof and an array-type transducer that forms a focus through an array of a plurality of transducers.

Conventional high-intensity focused ultrasound transducers are used to focus ultrasonic waves on a set focus, and generally use two methods to this end. A first method uses a single-element transducer, which is effective in focusing ultrasonic waves at a mechanically designed focus by giving a curvature to the surface of the transducer and generating heat. A second method uses an array-type transducer, and is a method of variably forming a focus through a time delay of an applied signal by arranging small-element transducers. Ultrasonic waves focused by a high-intensity focused ultrasound transducer make it possible to treat only an affected area locally while minimally affecting a part other than the focus. Thermal and mechanical energy at a focus is used to treat various lesions. In particular, high-intensity focused ultrasound transducers are mainly used in the field of benign tumor and cancer treatments, and have an advantage of not burdening a human body compared to direct surgery. Further, vibration and cavitation effects by high acoustic intensity may help to increase drug diffusion in blood, cells, and extracellular fluids, and have been recently used to maximize drug release by stimulating a structure, such as a microcarrier carrying a drug.

A transducer array generates a focus through positioning of a plurality of transducers and phase control of an applied signal, and forms a pressure field (e.g., twin-trap, vortex, or bottle-trap) suitable for particle trapping through a phase change. When particles exist inside the formed pressure field, the particles are trapped by acoustic radiation force in a low-pressure region. It is possible to drive particles in three dimensions through additional phase control or an external drive stage, and research on driving of a microstructure using this aspect is in progress in various fields.

However, conventional high-intensity ultrasound transducers may be limitedly used for purposes other than simply giving a stimulus or treating lesions, are not stable for use, such as capturing or moving particles, such as a microrobot, and form ultrasonic waves with an excessively higher intensity than necessary.

In addition, a conventional transducer array generates a relatively small ultrasonic intensity with the same power compared to a single-element high-intensity focused ultrasound transducer, and has insufficient efficiency in mechanical and thermal energy generated at the focus, thus being ineffective in being used for stimulating a drug delivery carrier.

Accordingly, there is a demand for development of a transducer array system having high mechanical and thermal energy efficiency in a focal region and capable of stably capturing particles.

DETAILED DESCRIPTION

Technical Problem

Therefore, inventors of the present disclosure have manufactured a transducer array system including a control unit to adjust a phase difference between a first transducer disposed at a center and a second transducer disposed to surround an outer circumference of the first transducer, and the transducer array system according to the present disclosure has been identified as having an outstandingly excellent effect of being capable of capturing microparticles through a low pressure inside a pressure field while focusing high-intensity ultrasonic waves in a focal region.

An aspect of the present disclosure is to provide a transducer array system including a control unit to adjust a phase difference between a first transducer and a second transducer disposed to surround an outer circumference of the first transducer.

Another aspect of the present disclosure is to provide a method for driving a microrobot.

Technical Solution

The present disclosure relates to an ultrasound-based microparticle trapping and stimulation device. A transducer array system according to the present disclosure may focus high-intensity ultrasonic waves, and may capture microparticles through a low pressure in a pressure field.

Hereinafter, the present disclosure will be described in more detail.

In accordance with an aspect of the present disclosure, there is provided a transducer array system including: a first transducer that includes a surface with a first curvature and is disposed to form a first focus in a central area or a peripheral area of an object; a second transducer that is disposed to surround an outer circumference of the first transducer and to form a second focus at the same position as that of the first focus; and a control unit that controls the first transducer and the second transducer by applying a signal to adjust a phase difference between the first transducer and the second transducer.

In an embodiment of the present disclosure, the control unit controls the phase difference between the first transducer and the second transducer to be 0 (0°) or π (180°).

In the transducer array system according to the present disclosure, the control unit may control the phase difference between the first transducer and the second transducer to be 0 (0°). As the phase difference is 0, ultrasonic waves of the first transducer and the second transducer may be concentrated in a focal region, thus focusing high-intensity ultrasonic waves. When the control unit controls the phase difference between the first transducer and the second transducer to be π (180°), the ultrasonic waves of the first transducer and the second transducer may be canceled in the focal region, thus forming a pressure field effective for microparticle capturing in the focus (see FIG. 5 to FIG. 9).

In an embodiment of the present disclosure, the transducer array system may further include a motor stage unit that adjusts a position of at least one of the first transducer, the second transducer, and the control unit.

In the present disclosure, the motor stage unit may move the first transducer and the second transducer along an x-axis or y-axis on the plane where the first transducer and the second transducer are positioned.

In the present disclosure, the "x-axis" denotes one axis on the plane where the first transducer and the second transducer are positioned, and the "y-axis" denotes an axis perpendicular to the x-axis on the plane where the first transducer and the second transducer are positioned.

In an embodiment of the present disclosure, the transducer array system may further include an interface.

In an embodiment of the present disclosure, the interface may include a material similar to human tissue, such as silicone.

In the transducer array system according to the present disclosure, the interface is for minimizing reflection of ultrasound according to a medium change, and may be used to function as a contact medium between the transducer array system and a human body. The interface may be filled with a liquid medium, such as a gel applied in an ultrasound, to remove an air layer between an ultrasonic transducer and the interface. An outer surface of the silicone, to which gel is applied, may come in contact with the human body to minimize a reflection effect due to a medium change during the ultrasound.

In an embodiment of the present disclosure, the second transducer may include a surface with a second curvature, and may have a toroidal shape disposed to surround an outside of the first transducer.

In an embodiment of the present disclosure, the second transducer may include at least one planar transducer including a plane surface and forming a focus at the same position as that of the second focus.

In an embodiment of the present disclosure, the second transducer may include 10 to 20 planar transducers, and may include, for example, 15 planar transducers, without being limited thereto.

In an embodiment of the present disclosure, the first transducer may be a high-intensity focused ultrasound (HIFU) transducer. Accordingly, the transducer array system according to the present disclosure may concentrate high-intensity ultrasonic waves in the focal region while capturing microparticles in the focal region through a low pressure field.

In an embodiment of the present disclosure, the object may be a microrobot or a drug delivery carrier.

As used herein, the term "microrobot" is a type of body-insertable medical device, and may include a mechanical/electronic microrobot including a permanent magnet or an elongated body as a millimeter-size magnetic body, such as a vascular robot and an active capsule endoscope, and a macromolecular/cell-based microrobot including magnetic nanoparticles as a micro/nano-size magnetic body, such as a microcarrier for a DDS, a microscaffold for cell therapy product delivery, a nanorobot, and a macrophage robot, and may include other types of microrobots.

The microrobot according to the present disclosure may further include at least one selected from a group including a camera module, a position information providing unit, a driving unit, a treatment unit, a robot control unit, a data transmission/reception unit, and a wireless power reception unit.

The microrobot according to an embodiment of the present disclosure does not need to be manufactured by a specific method or to include a specific component, which is an advantage of ultrasonic driving of the present disclosure, and using a driving system of the present disclosure makes it possible to capture a control object regardless of the type or component of the control object. When particles of any material have a higher density than a medium in an acoustic field, a characteristic of acoustic radiation force makes it possible to capture the particles by the transducer array system and a phase control method of the present disclosure. The microrobot of the present disclosure, that is, an object to be captured, is preferably a particle having a diameter smaller than a wavelength of a frequency used for ultrasonic driving. Generally, a particle with a diameter smaller than a half wavelength may be stably captured. In a specific example, nanoparticles and microparticles having a diameter much smaller than an ultrasonic wavelength used in a transducer and having a higher density than a fluid medium in an acoustic field may be stably captured.

In accordance with another aspect of the present disclosure, there is provided a method for driving a microrobot including a position control operation of controlling a position of a microrobot through ultrasonic waves by driving a transducer array system.

The transducer array system includes: a first transducer that includes a surface with a first curvature and is disposed to form a first focus in a central area or a peripheral area of an object; a second transducer that is disposed to surround an outer circumference of the first transducer and to form a second focus at the same position as that of the first focus; and a control unit that controls the first transducer and the second transducer by applying a signal to adjust a phase difference between the first transducer and the second transducer.

In an embodiment of the present disclosure, the control unit may control the phase difference between the first transducer and the second transducer to be 0 or $\pi$.

In an embodiment of the present disclosure, the transducer array system may further include a motor stage unit that adjusts a position of at least one of the first transducer, the second transducer, and the control unit.

In an embodiment of the present disclosure, the motor stage unit may adjust the position on the same plane as the first transducer and the second transducer.

In the present disclosure, the motor stage unit may move the first transducer and the second transducer along the x-axis or y-axis on the plane where the first transducer and the second transducer are positioned.

In an embodiment of the present disclosure, the second transducer may include a surface with a second curvature, and may have a toroidal shape disposed to surround an outside of the first transducer.

In an embodiment of the present disclosure, the second curvature may be the same as the first curvature.

In an embodiment of the present disclosure, the second transducer may include at least one planar transducer including a plane surface and forming a focus at the same position as that of the second focus.

In an embodiment of the present disclosure, the first transducer may be a high-intensity focused ultrasound (HIFU) transducer.

Advantageous Effects

The present disclosure relates to an ultrasound-based microparticle trapping and stimulation device. A transducer array system according to the present disclosure may focus high-intensity ultrasonic waves in a focal region, and has an outstandingly excellent capability to capture microparticles through a low pressure in a pressure field, thus being used in various medical fields.

BEST MODE FOR CARRYING OUT THE INVENTION

A transducer array system including:
a first transducer that includes a surface with a first curvature and is disposed to form a first focus in a central area or a peripheral area of an object;
a second transducer that is disposed to surround an outer circumference of the first transducer and to form a second focus at the same position as that of the first focus; and
a control unit that controls the first transducer and the second transducer by applying a signal to adjust a phase difference between the first transducer and the second transducer.

MODE FOR CARRYING OUT THE INVENTION

The above aspects, features, and advantages will be more apparent from the following detailed description taken in conjunction with the accompanying drawings, and accordingly those skilled in the art to which the present disclosure belongs may easily implement the technical idea of the present disclosure. When detailed descriptions about known technology related to the present disclosure are determined to make the gist of the present disclosure unclear in describing the present disclosure, the detailed descriptions will be omitted herein.

In the present specification, the expression that a part "comprises or includes" an element means that the part does not exclude another element but may further include another element unless specified otherwise. As used herein, the term "unit" refers to a unit of processing at least one function or operation, which may be configured as hardware, software, or a combination of hardware and software. In the context of describing the present disclosure, "a" or "an", "one", and equivalent expressions may be used to inclusively refer to a singular form or a plural form unless indicated otherwise or clearly contradicted by context herein.

It should be understood that when an element is referred to as being "connected" or "coupled" to another element, the element may be connected or coupled directly to the other element or any other element may be interposed therebetween. In contrast, it should be understood that when an element is referred to as being "directly connected" or "directly coupled" to another element, there is no element interposed therebetween. Other expressions describing a relationship between elements, such as "between" and "directly between" or "adjacent to" and "directly adjacent to" should be interpreted similarly.

Figure 1:
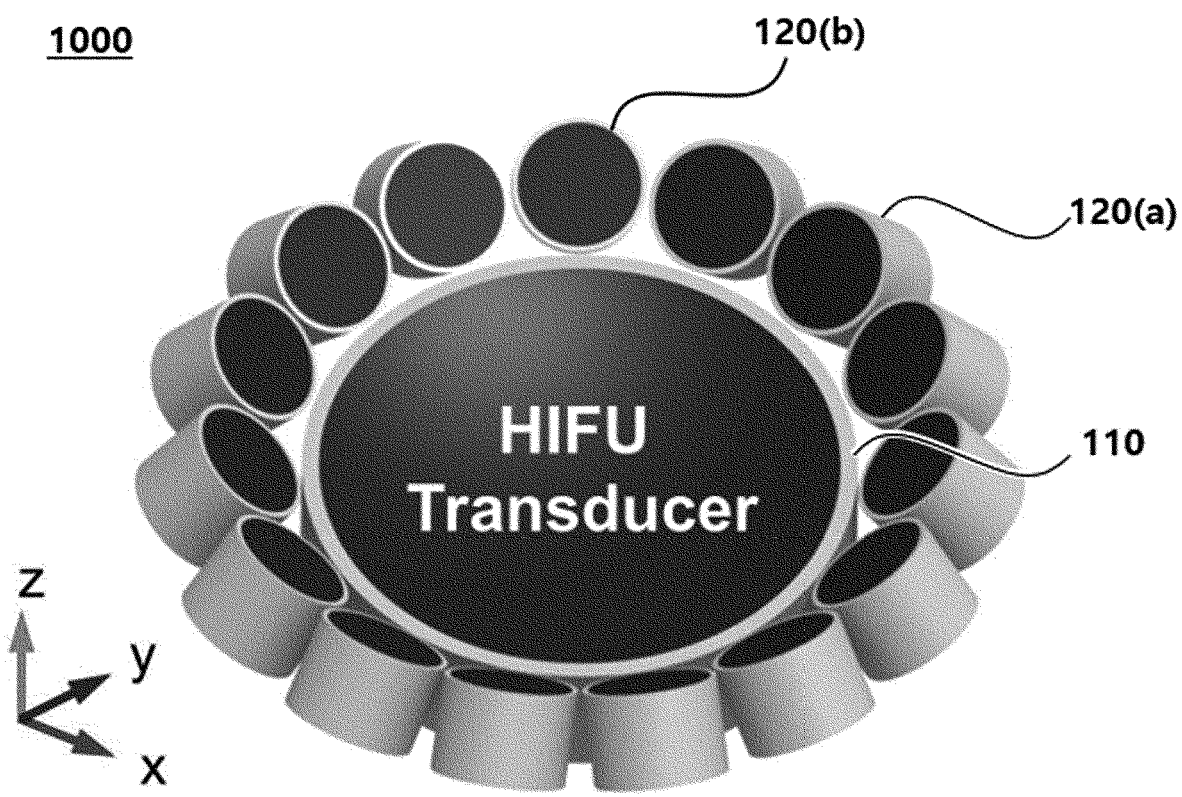
FIG. 1 is a perspective view of a transducer array system according to an embodiment of the present disclosure.
Figure 2:
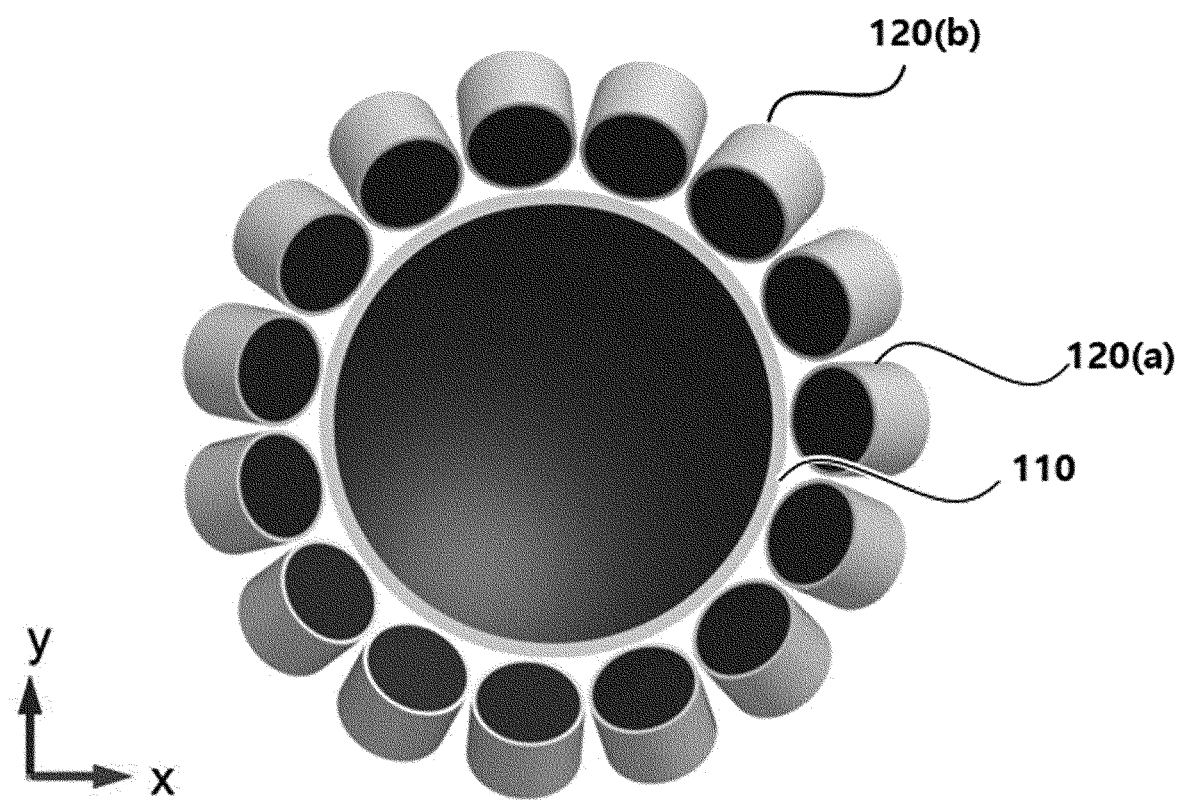
FIG. 2 is a top view of a transducer array system according to the embodiment of the present disclosure.

FIG. 1 is a perspective view of a transducer array system according to an embodiment of the present disclosure, and FIG. 2 is a top view of the transducer array system according to the embodiment of the present disclosure.

Referring to FIG. 1 and FIG. 2, the transducer array system 1000 according to the embodiment may include a first transducer 110 and second transducers 120 (a) and 120 (b).

The first transducer 110 may be a high-intensity focused ultrasound (HIFU) transducer.

The second transducers 120 (a) and 120 (b) may be planar transducers, and may be disposed to form a second focus near to or at the same position as that of a first focus, which is a focus of the first transducer 110.

The second transducers 120 (a) and 120 (b) may include at least one planar transducer including a plane surface and forming a focus at the same position as that of the second focus. The second transducers 120 (a) and 120 (b) may be disposed to be spaced at a predetermined interval around the first transducer 110, and a plurality of second transducers 120 (a) and 120 (b) may be disposed from each other at a predetermined interval. The second transducers 120 (a) and 120 (b) may include 10 to 20 planar transducers, and may include, for example, 15 planar transducers as illustrated in FIG. 1 and FIG. 2.

The transducer array system 1000 according to the embodiment may further include a control unit (not shown) in addition to the first transducer and the second transducer.

The control unit may transmit a command or a signal to control at least one of the first transducer, the second transducer, a motor stage unit, and an interface of the transducer array system according to the embodiment to each module or each unit, or may receive and process a signal or information collected from each module or each unit.

Specifically, the control unit may apply a signal to adjust a phase difference between the first transducer 110 and the second transducers 120 (a) and 120 (b), thereby controlling the first transducer 120 (a) and 120 (b) and the second transducer. For example, the control unit may control the phase difference between the first transducer 110 and the second transducers 120 (a) and 120 (b) to be 0 or π.

A phase of each of the first transducer 110 and the second transducers 120 (a) and 120 (b) may be independently controlled.

The transducer array system 1000 according to the embodiment may further include the motor stage unit (not shown). The motor stage unit may adjust positions of the first transducer 110 and the second transducers 120 (a) and 120 (b) on the same plane. Specifically, the motor stage unit may move the first transducer and the second transducers along an x-axis or y-axis on the plane where the first transducer 110 and the second transducers 120 (a) and 120 (b) are positioned.

The transducer array system 1000 according to the embodiment may further include the interface (not shown). The interface may include a material similar to human tissue, such as silicone. The interface is for minimizing reflection of ultrasound according to a medium change, and may be used to function as a contact medium between the transducer array system and a human body.

Figure 3:
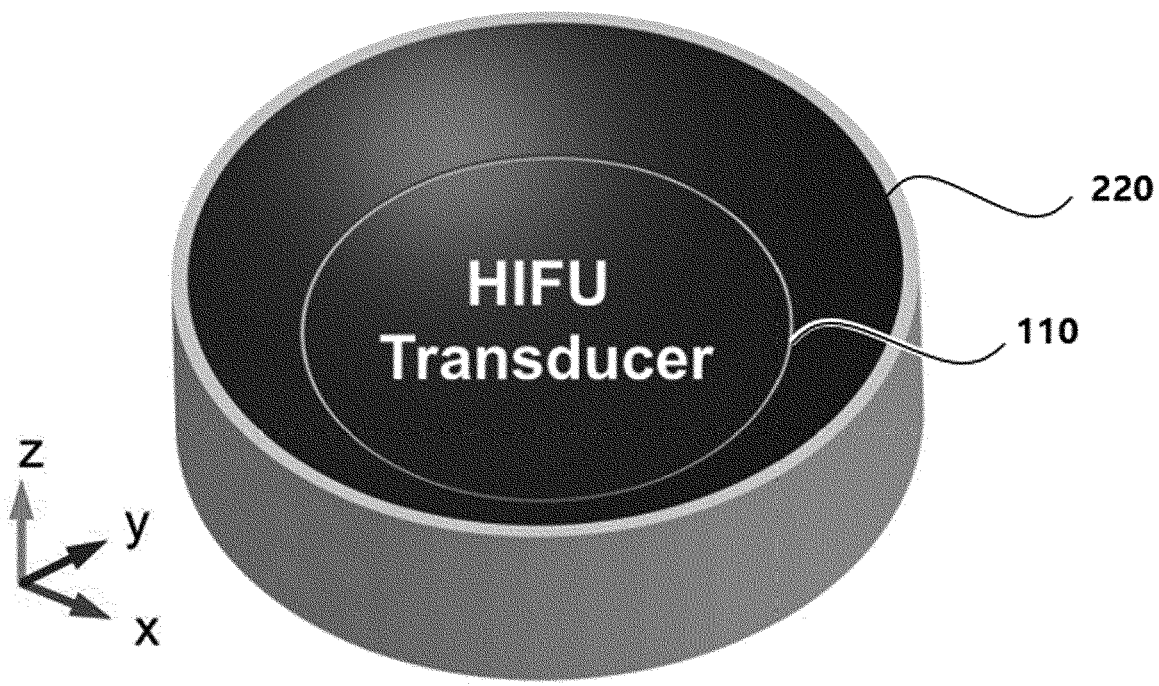
FIG. 3 is a perspective view of a transducer array system according to another embodiment of the present disclosure.
Figure 4:
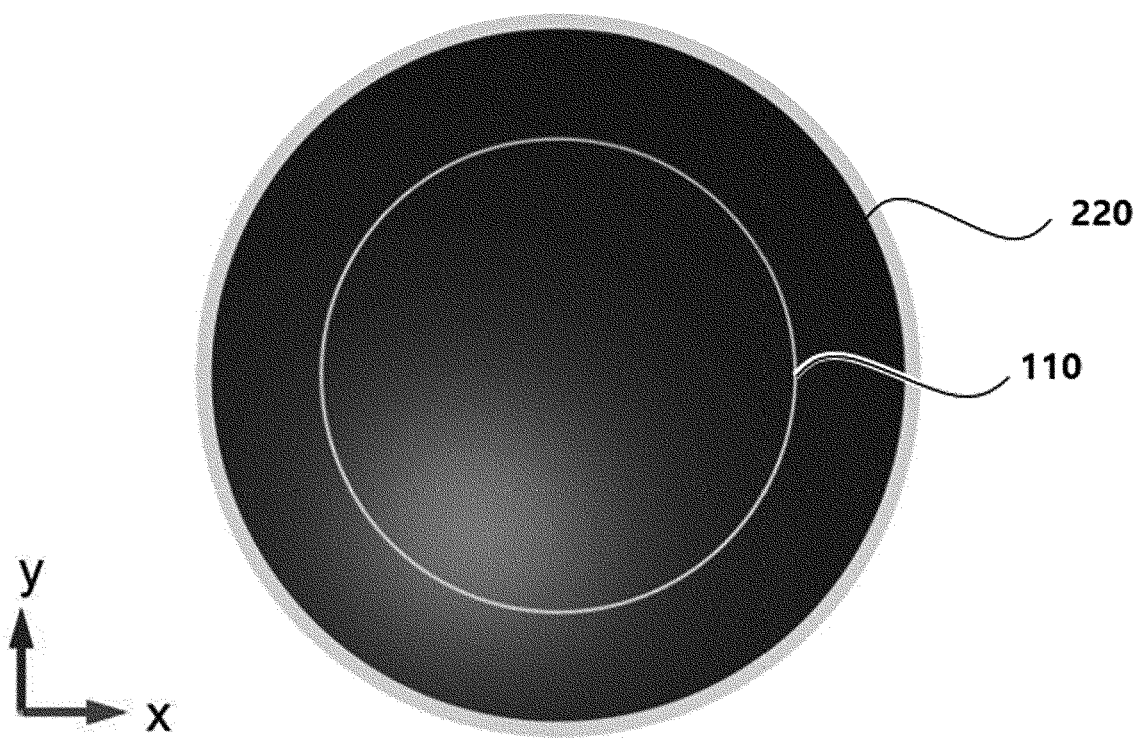
FIG. 4 is a top view of a transducer array system according to the other embodiment of the present disclosure.

FIG. 3 is a perspective view of a transducer array system according to another embodiment of the present disclosure, and FIG. 4 is a top view of the transducer array system according to the other embodiment of the present disclosure.

Referring to FIG. 3 and FIG. 4, the transducer array system 2000 according to the other embodiment may include a first transducer 110 and a second transducer 220.

In the transducer array system 2000 according to the other embodiment, the second transducer 220 may include a surface having a second curvature, and may have a toroidal shape disposed to surround an outside of the first transducer 110. Here, to match a focus of the first transducer 110 and a focus of the second transducer 220, the second curvature may be the same as a first curvature.

Figure 5:
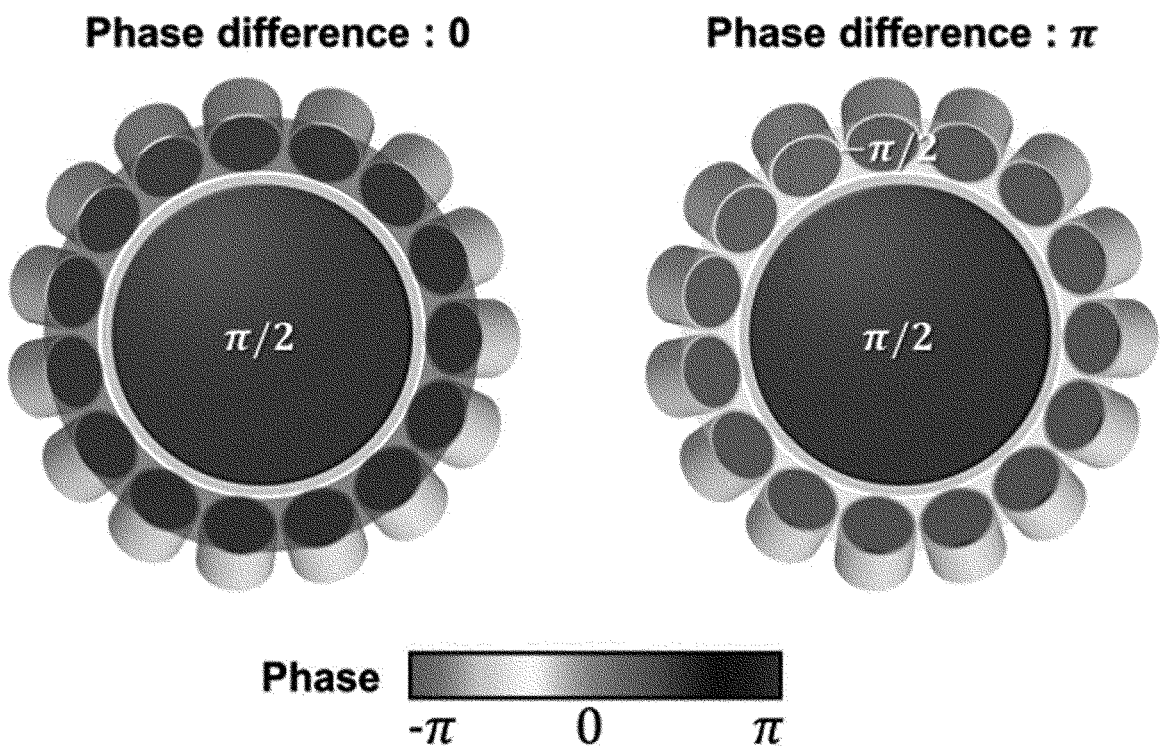
FIG. 5 illustrates a phase difference between a first transducer and a second transducer in the transducer array system according to the embodiment of the present disclosure.
Figure 6:
FIG. 6 illustrates a phase difference between a first transducer and a second transducer in the transducer array system according to the other embodiment of the present disclosure.
Figure 6:
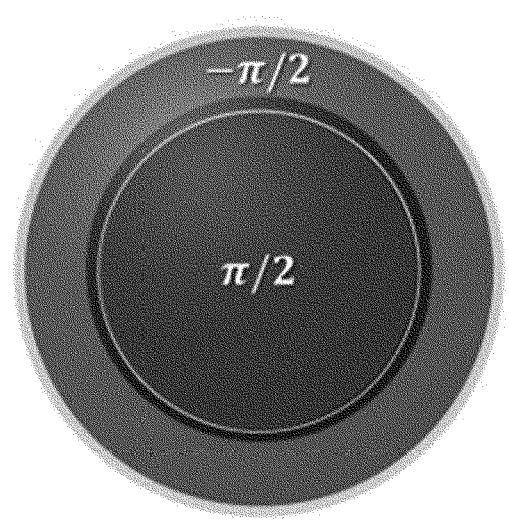
Figure 6:
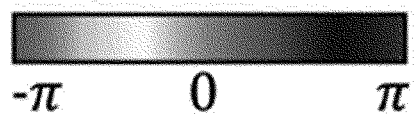
Figure 7:
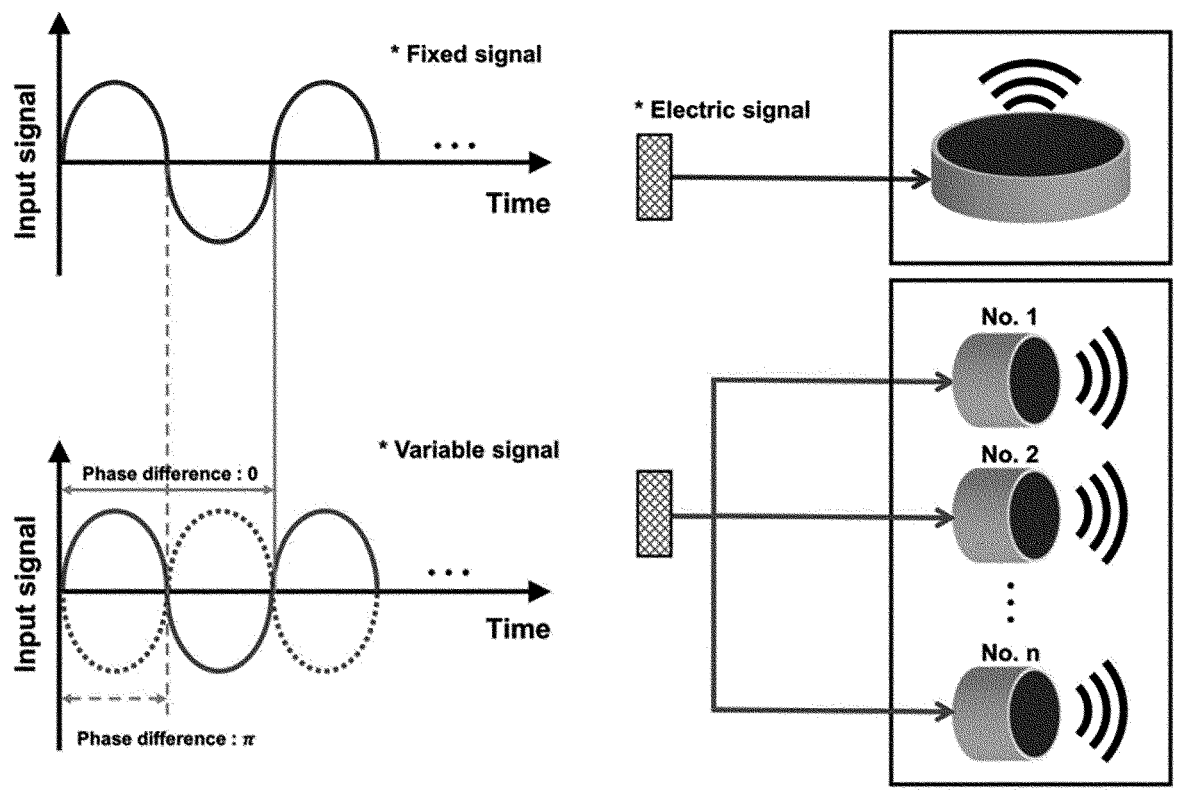
FIG. 7 is a graph illustrating the phase difference between the first transducer and the second transducer in the transducer array system according to the embodiment of the present disclosure.

FIG. 5 illustrates a phase difference between the first transducer and the second transducer in the transducer array system according to the embodiment of the present disclosure, FIG. 6 illustrates a phase difference between the first transducer and the second transducer in the transducer array system according to the other embodiment of the present disclosure, and FIG. 7 is a graph illustrating the phase difference between the first transducer and the second transducer in the transducer array system according to the embodiment of the present disclosure.

Referring to FIG. 5 to FIG. 7, in the transducer 1000 according to one embodiment and the transducer 2000 according to another embodiment, the phase difference between the first transducer and the second transducer may be controlled to be between $-\pi$ and $\pi$. For example, the phase difference between the first transducer and the second transducer may be controlled to be 0 or π.

For example, as illustrated in FIG. 5 and FIG. 6, the phase difference between the two transducers may be controlled to be 0 (0°) by maintaining a phase of the first transducer at $\pi/2$ and maintaining a phase of the second transducer at $\pi/2$. Alternatively, the phase difference between the two transducers may be controlled to be π (180°) by maintaining the phase of the first transducer at $\pi/2$ and maintaining the phase of the second transducer at $-\pi/2$.

The phase difference between the transducers may be controlled through a time delay of a signal transmitted to each transducer. The time delay is for generating a phase difference between applied signals applied to the transducers, and a position of a focus is not changed simply by differently setting a time delay. When a sine wave is applied as an applied signal and one cycle of the signal is $2\pi$, a position change of the focus may be controlled by changing a phase of the applied signal within $2\pi$ through a time delay as illustrated in FIG. 7.

Figure 8:
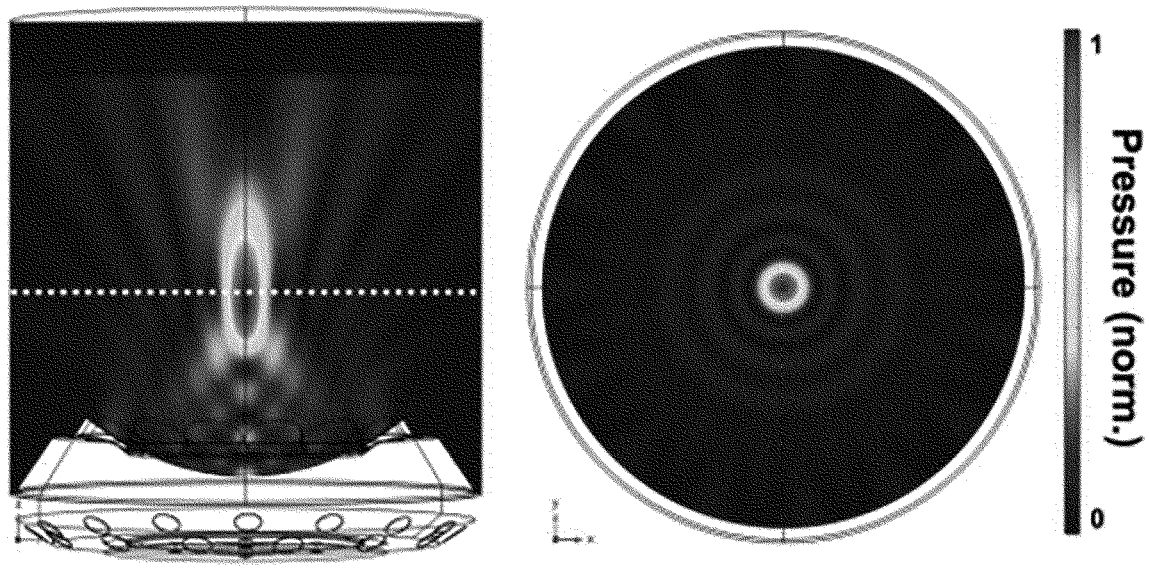
FIG. 8 illustrates an intensity of ultrasonic waves and a pressure field in a focal region according to the phase difference between the first transducer and the second transducer in the transducer array system according to the embodiment of the present disclosure.
Figure 8:
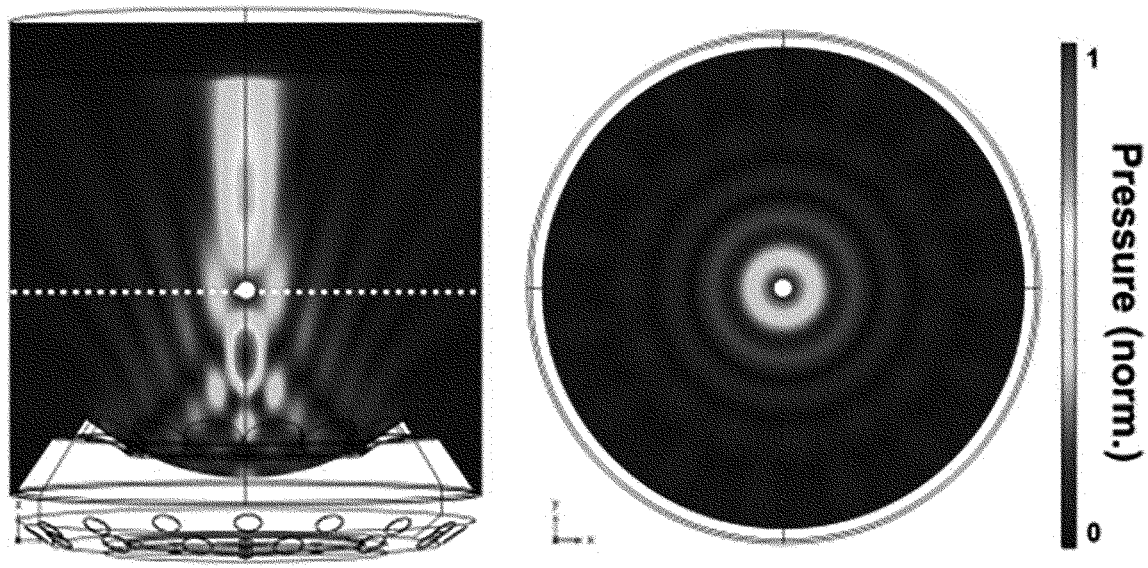
Figure 9:
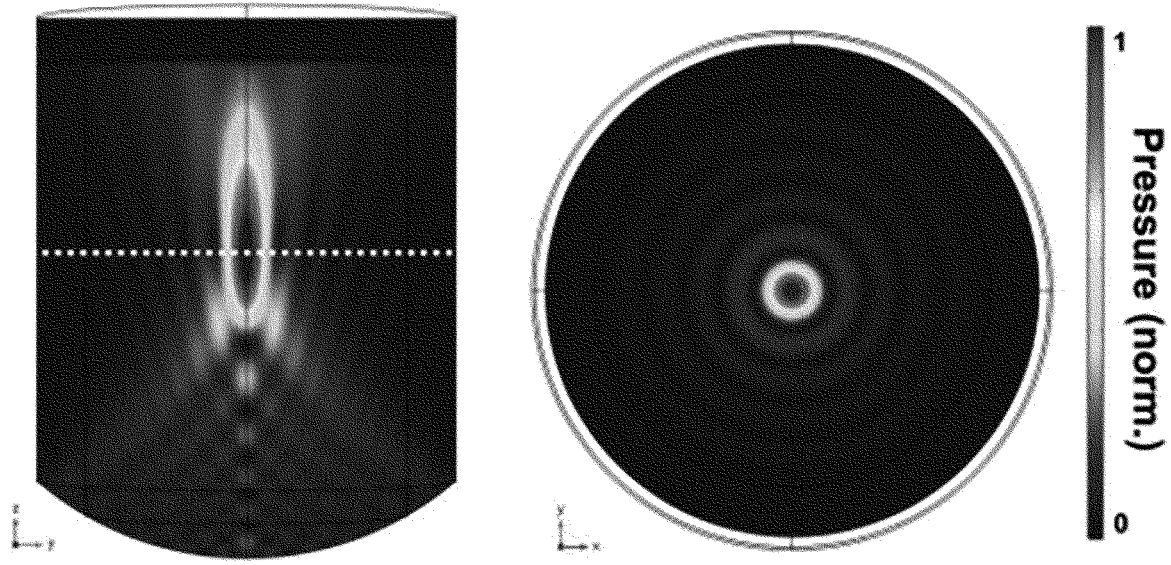
FIG. 9 illustrates an intensity of ultrasonic waves and a pressure field in a focal region according to the phase difference between the first transducer and the second transducer in the transducer array system according to the other embodiment of the present disclosure.
Figure 9:
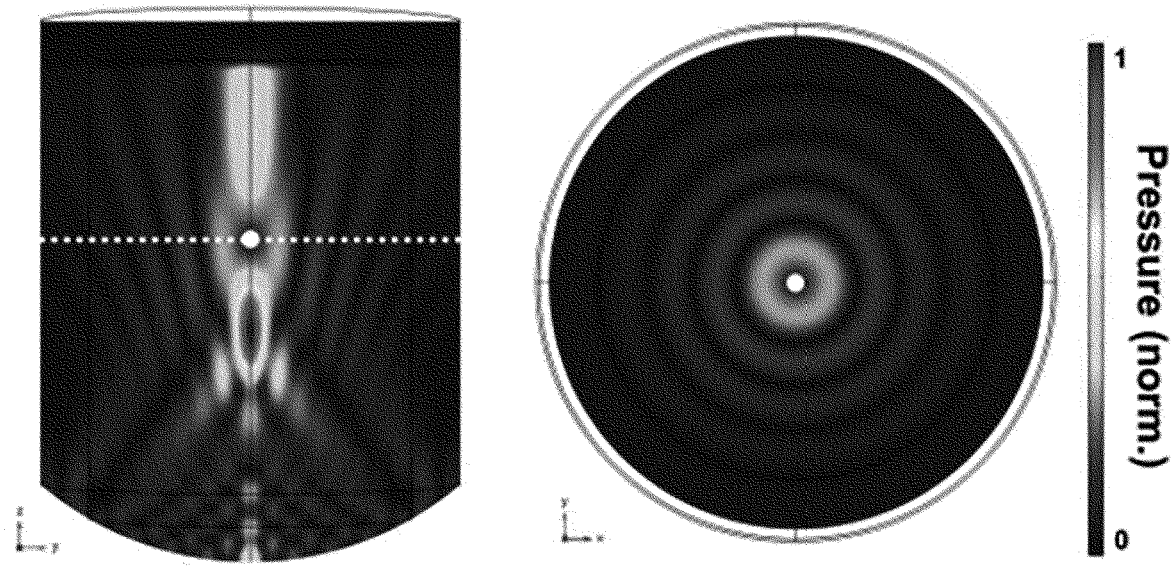

FIG. 8 illustrates an intensity of ultrasonic waves and a pressure field in a focal region according to the phase difference between the first transducer and the second transducer in the transducer array system according to the embodiment of the present disclosure, and FIG. 9 illustrates an intensity of ultrasonic waves and a pressure field in a focal region according to the phase difference between the first transducer and the second transducer in the transducer array system according to the other embodiment of the present disclosure.

Referring to FIG. 8 and FIG. 9, the transducer array system 1000 according to the embodiment and the transducer array system 2000 according to the other embodiment may focus strong ultrasonic waves on the focus or may form a low pressure field effective for microparticle trapping by using the phase difference between the first transducer and the second transducer.

For example, referring to FIG. 8, the transducer array system 1000 according to the embodiment may control the phase difference between the first transducer and the second transducer to be 0, thereby focusing ultrasonic waves to have a strong intensity in the focal region of the first transducer and the second transducer having the same focus. The transducer array system according to the embodiment may be used for benign tumor and cancer treatments without affecting the human body by generating thermal and mechanical energy in the focal region, and may maximize drug release in the focal region by stimulating a structure, such as a microcarrier, through vibration and cavitation effects caused by high acoustic intensity.

The transducer array system 1000 according to the embodiment may control the phase difference between the first transducer and the second transducer to be IT to cancel ultrasonic waves in the focal region of the first transducer and the second transducer having the same focus, thereby forming a pressure field having a low pressure in the focal region. As the pressure field having the low pressure is formed in the focal region, a user may capture (traps) microparticles with a predetermined size or smaller by locating the microparticles in the focal region of the transducer array system. For example, the user may capture the microrobot in the focal region to drive a microrobot, and may also capture particles, such as micro-drug carriers, in the focal region.

As described above, a transducer system according to the present disclosure may independently control phases of a first transducer and a second transducer, and accordingly a user may freely control a phase difference between the first transducer and the second transducer. Therefore, the user may form a node region with a low pressure in the focal region to collect drug carriers by controlling the phase difference between the first transducer and the second transducer to be TT, and may then concentrate thermal and mechanical energy in the focal region to induce drug release through vibration and cavitation effects by controlling the phase difference between the transducer and the second transducer back to be 0.

Hereinafter, the present disclosure will be described in more detail with reference to examples. These examples are only for explaining the present disclosure in more detail, and it will be apparent to those skilled in the art that the scope of the present disclosure is not limited by these examples according to the gist of the present disclosure.

Preparation Example: Manufacture of Transducer Array System

Figure 10:
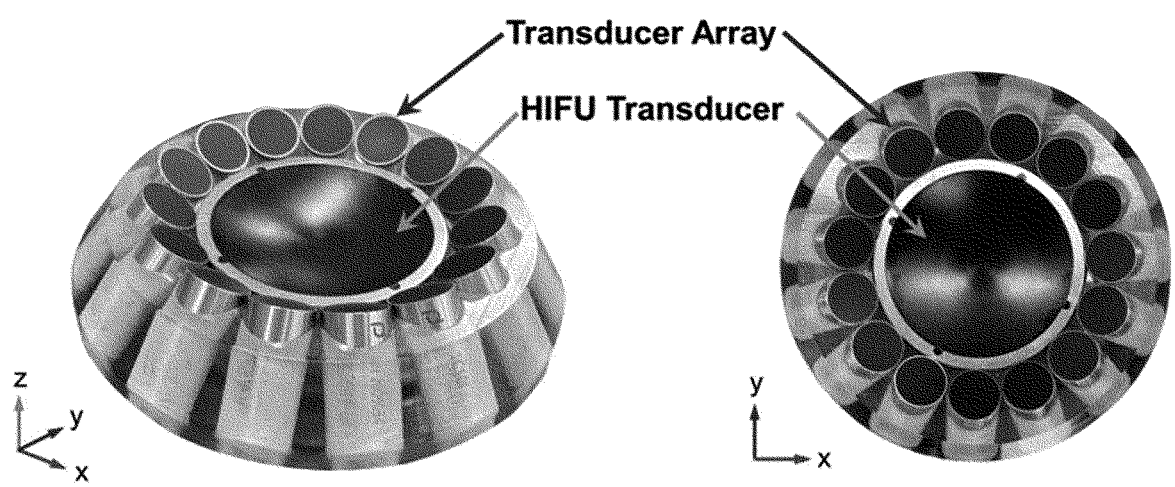
FIG. 10 is a photograph of a transducer array system manufactured according to an embodiment of the present disclosure.

To examine a microparticle capture capability of a transducer array system according to the present disclosure, a transducer array system was manufactured. As illustrated in FIG. 10, in the transducer array system, a high-intensity focused ultrasound (HIFU) transducer having a diameter of 60 mm and a curve with a focal distance of 58 mm was placed in the center, and 15 planar ultrasonic transducers with a diameter of 16 mm were placed around the high-intensity focused ultrasound transducer.

Example: Verification of Microparticle Capture Capability

The transducer array system manufactured in the preparation example was placed inside a water tank filled with water, and sine-wave signals having a frequency of 1 MHz and having opposite phases were applied to the respective transducers to generate ultrasonic waves. Used microparticles were particles with a diameter of 300 μm, which were dropped into a focal region of the transducer array system, and a trapping result was identified.

Figure 11:
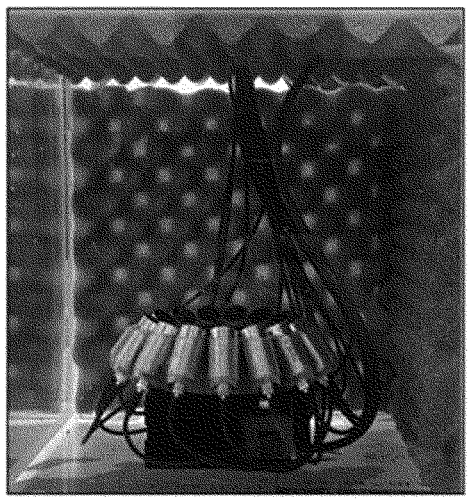
FIG. 11 illustrates a microparticle capture capability of the transducer array system manufactured according to the embodiment of the present disclosure.
Figure 11:
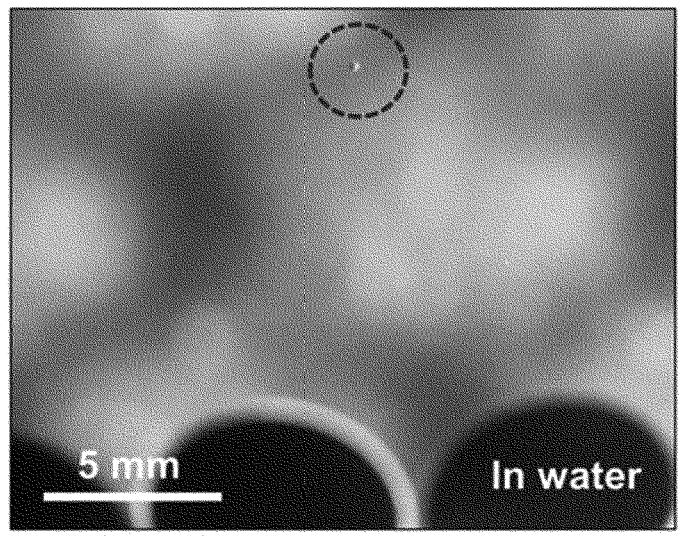

As a result of an experiment, as illustrated in FIG. 11, microparticles were identified to be captured in the focal region of the transducer array system according to the present disclosure.

INDUSTRIAL APPLICABILITY

The present disclosure relates to an ultrasound-based microparticle trapping and stimulation device and, more particularly, to a device for trapping or stimulating microparticles by adjusting a phase difference between a first transducer disposed in a central area and a second transducer disposed to surround an outer circumference of the first transducer.

What is claimed is:
1. A transducer array system comprising:
a first transducer that comprises a surface with a first curvature and is disposed to form a first focus in a central area or a peripheral area of an object;
a second transducer that is disposed to surround an outer circumference of the first transducer and to form a second focus at a position that is the same as the first focus;
a control unit configured to control the first transducer and the second transducer by applying a signal to adjust a phase difference between the first transducer and the second transducer; and
a motor stage unit configured to adjust a position of the first transducer and the second transducer,
wherein the control unit is configured to control the phase difference between the first transducer and the second transducer to be 0 (0°) or π (180°).

2. The transducer array system as claimed in claim 1, wherein the motor stage unit is configured to adjust the position of the first transducer and the second transducer along the same plane.

3. The transducer array system as claimed in claim 1, wherein the second transducer comprises a surface with a second curvature, and has a toroidal shape disposed to surround an outside of the first transducer.

4. The transducer array system as claimed in claim 3, wherein the second curvature is the same as the first curvature.

5. The transducer array system as claimed in claim 1, wherein the second transducer comprises at least one planar transducer comprising a plane surface and forming a focus at the same position as the first focus.

6. The transducer array system as claimed in claim 1, wherein the first transducer is a high-intensity focused ultrasound (HIFU) transducer.

7. The transducer array system as claimed in claim 1, wherein the object is a microrobot or a drug delivery carrier.

8. A method for driving a microrobot, the method comprising:
a position control operation of controlling a position of a microrobot through ultrasonic waves by driving a transducer array system,
wherein the transducer array system comprises:
a first transducer that comprises a surface with a first curvature and is disposed to form a first focus in a central area or a peripheral area of an object;
a second transducer that is disposed to surround an outer circumference of the first transducer and to form a second focus at a position that is the same as the first focus;
a control unit configured to control the first transducer and the second transducer by applying a signal to adjust a phase difference between the first transducer and the second transducer; and
a motor stage unit configured to adjust a position of the first transducer and the second transducer, wherein the control unit is configured to control the phase difference between the first transducer and the second transducer to be 0 (0°) or π (180°).

9. The method as claimed in claim 8, wherein the second transducer comprises a surface with a second curvature and has a toroidal shape disposed to surround an outside of the first transducer.

10. The method as claimed in claim 9, wherein the second curvature is the same as the first curvature.

11. The method as claimed in claim 8, wherein the second transducer comprises at least one planar transducer comprising a plane surface and forming a focus at the same position as the first focus.

12. The method as claimed in claim 8, wherein the first transducer is a high-intensity focused ultrasound (HIFU) transducer.

* * * * *